United States Patent [19]
Alderete et al.

[11] Patent Number: 4,894,328
[45] Date of Patent: Jan. 16, 1990

[54] IMMUNODIAGNOSTIC TEST FOR SYPHILIS AND OTHER TREPONEMAL INFECTIONS

[75] Inventors: John F. Alderete; Joel B. Baseman, both of San Antonio, Tex.

[73] Assignee: Board of Regents, The University of Texas System, Austin, Tex.

[21] Appl. No.: 46,277

[22] Filed: May 4, 1987

Related U.S. Application Data

[63] Continuation of Ser. No. 844,340, Mar. 26, 1986, abandoned, which is a continuation of Ser. No. 498,751, May 27, 1983, abandoned.

[51] Int. Cl.[4] .................. G01N 33/53; G01N 33/552; G01N 33/544; C07K 15/14
[52] U.S. Cl. ........................................ 435/7; 435/805; 435/810; 436/511; 436/527; 436/530; 436/534; 436/808; 436/809; 436/810; 530/395; 530/806; 530/811; 530/812; 530/814; 530/815; 530/825
[58] Field of Search ................. 435/4, 7, 21, 188, 253, 435/510, 511, 518, 535, 543, 547, 800, 804, 808–810, 811, 816, 819, 823, 824, 805; 424/85, 88, 94; 436/511, 527, 530, 534, 808, 810, 809; 530/395, 811, 812, 814, 815, 806, 825

[56] References Cited

U.S. PATENT DOCUMENTS

| | | | |
|---|---|---|---|
| 4,315,906 | 2/1982 | Gelder | 424/1.1 |
| 4,325,867 | 4/1982 | Eberle | 530/392 |
| 4,341,764 | 7/1982 | Wallace | 424/101 |
| 4,391,749 | 7/1983 | Engvall | 530/356 |
| 4,412,990 | 11/1983 | Lundblad | 514/21 |
| 4,440,679 | 4/1984 | Fernandes | 530/363 |
| 4,440,860 | 4/1984 | Klagsburn | 435/240 |
| 4,443,546 | 4/1984 | Stemerman | 435/240 |
| 4,444,206 | 4/1984 | Gold | 128/784 |
| 4,446,234 | 5/1984 | Russo | 435/29 |
| 4,453,939 | 6/1984 | Zimmerman | 604/368 |
| 4,455,300 | 6/1984 | Wallace et al. | 424/101 |
| 4,514,498 | 4/1985 | Kettman et al. | 935/103 |
| 4,740,467 | 4/1988 | Kettman et al. | 436/548 |
| 4,803,155 | 2/1989 | Petersen et al. | 436/518 |

OTHER PUBLICATIONS

Julkunen et al., "Interaction of Viral Envelope Glycoproteins with Fibronectin"; Infection and Immunity, (Jun. 1983).
Yamada et al, Nature, vol. 75, pp. 179-185, 1978.
Simpson et al, Infection and Immunity, vol. 39, pp. 275-279, 1983.
DeWater et al, Science, vol. 220, pp. 201-204, 1983.
Smith et al, Principles of Biochemistry: General Aspects, 1983, p. 466, editors: Laufer et al.
Baseman, J. B. et al, Infection and Immunity, 27:260 (1-1980).
Baseman, J. B. et al, Journal of Experimental Medicine, 151:573 (3-1980).
Alderette, J. F. et al, British Journal of Venereal Disease, 57:302-308 (4-1981).
Metzger et al, Immunology Today, 3:58 (3-1982).
Hayes et al, Infection and Immunity, 17:174-186 (7-1977).
Baseman, J. B. et al, Microbiology, pp. 203-207 (1979).
Alberts, B. et al, Molecular Biology of the Cell, pp. 692-715, Garland Publishing, N.Y. (1983).
Hynes, R. O. et al, Journal of Cell Biology, vol. 95, pp. 369-377 (11-1982).
Baseman, J. B. et al, The Parasitic Strategies of Treponema Pallidum, pp. 229-238 (1983).
Morrison-Plummer et al, British Journal of Venereal Diseases, 59:75-79 (1983).
Klebe, R. J., Journal of Cellular Physiology, 109:481-488 (1981).
Peterson, K. M. et al, Abstr. Annu. Meet. Am. Soc. Microbiol., 83:43 (3-1983), Abstract B121.
Rice, M. et al, Abstr. Annu. Meet. Am. Soc. Microbiol., 83:81 (3-1983), Abstract E28.

Primary Examiner—Robert J. Warden
Assistant Examiner—Florina B. Hoffer
Attorney, Agent, or Firm—Arnold, White & Durkee

[57] ABSTRACT

A component for the rapid detection of anti-Treponema pallidum antibodies adapted for use as a selective foundation material in standard immunoassays is provided. The component comprises a quantity of fibronectin insolubilized to a solid matrix. The fibronectin component provides a foundation material for the selective binding of antigenic outer membrane proteins extracted from Treponema pallidum. Incorporation of the insolubilized fibronectin component bound to the antigenic outer membrane proteins extracted from Treponema pallidum into a standard immunoassay test pack provides an immunological assay for the presence of respective complementary anti-Treponema pallidum antibody in a biological sample.

11 Claims, No Drawings

IMMUNODIAGNOSTIC TEST FOR SYPHILIS AND OTHER TREPONEMAL INFECTIONS

This is continuation of co-pending application Ser. No. 844,340 filed Mar. 26, 1986 which was a continuation of Ser. No. 498,751 filed May 27, 1983, both now abandoned.

BACKGROUND OF THE INVENTION

The present invention relates to immunological diagnostic assays; and more particularly it relates to immunological diagnostic tests for syphilis and related treponemal infections.

Syphilis is a unique disease associated with a complex host response which may be accompanied by intermittent periods of latency and classical stage development. Neither protective immunogens nor mechanisms of host resistance have been clearly defined. Also, little information is available concerning the biological-chemical properties of *T. pallidum* that relate to virulence. The limitations of the model system, including the inability to sequentially in vitro passage virulent treponemes, represent serious experimental deficiencies in developing potential diagnostic assays and vaccinogens. Currently available immunodiagnosis assays for syphilis are inadequate. Routinely, a "non-specific" screening test (VDRL, cardiolipin antigen) is used which causes many false-positive reactions. For example, numerous infections and autoimmune disorders as well as syphilis cause increases in the detected anti-cardiolipin antibodies. Also, this test fails to identify significant numbers of syphilis-positive test samples. Furthermore, the antigen-specific test for confirmation of syphilis is most often the FTA-ABS slide test which requires whole organisms, fluoresceinconjugated reagents and fluorescence microscopy, which involves a time-consuming, expensive and qualitative assay. Therefore millions of serodiagnostic tests are performed each year in the U.S. alone under clearly suboptimal assay conditions resulting in a tremendous economic and emotional burden in our population. In addition, immuno-diagnosis of pinta and yaws (other human treponemal diseases) is unsatisfactory.

The present invention should markedly assist in improved diagnosis of these treponemal infections. The Applicants have evolved a strategy that permits identification and characterization of *T. pallidum* virulence determinants which are believed to be present in syphilis and these other pathogenic spirochetes. As an outcome of this strategy, Applicants have devised a rational and experimentally effective method for serodiagnosis of syphilis and related treponemal infections that can be used routinely with greatly improve specificity.

SUMMARY OF THE INVENTION

This invention provides a component for the rapid detection of anti-treponemal antibodies or treponemal immunogenic proteins in body fluids which component is adapted for use as the selective foundation agent in standard immunodiagnostic assay techniques.

In accordance with this invention a component for a diagnostic test pack useful for the immunological detection of treponemal protein immunogens in body fluids or antibodies specific for treponemal protein immunogens is provided. The component comprises a quantity of fibronectin protein adhered to an insoluble support matrix. In some applications of immunological assays techniques such as for the detection of anti-treponemal antibodies in a biological sample, it is desirable that the component of fibronectin adhered to the insoluble support matrix further includes treponemal protein immunogens bound to the fibronectin protein.

The fibronectin component thus provided serves as a selective foundation material adapted for use in a variety of standard immunoassay systems, such as radioimmunoassays, enzyme linked immunosorbent assays, and fluorescent tagged immunoassays. By employing the fibronectin component of the present invention in the standard immunoassays systems, there is provided a rapid, simple, reliable and sensitive immunoassay for the detection of either anti-treponemal antibodies or treponemal immunogenic proteins present in a biological sample. The presence of either anti-treponemal antibodies or treponemal immunogenic proteins in a biological sample, such as blood serum taken from a host, is an indication of treponemal infection of the host system.

DETAILED DESCRIPTION OF THE PREFERRED EMBODIMENT

The invention will be described in terms of preferred embodiments which represent the best mode known to the inventors at the time of this application.

The present invention provides an immunodiagnostic assay for syphilis and other infections such as yaws and pinta caused by closely related spirochetes. The causative organism of these diseases resides with the bacterial Treponema family, namely *Treponema pallidum* (syphilis), *Treponema pertenue* (yaws) and *Treponema carateum* (pinta). The present invention encompasses the use of fibronectin protein as a selective receptor for the adhesion of specific immunogenic treponemal proteins. Fibronectin protein when adhered to an insoluble support matrix provides a reactive foundation for immunodiagnostic assays effective to detect either treponemal protein immunogens or anti-treponemal antibodies present in biological liquid samples.

Fibronectin (mW 450,000) is an adhesive glycoprotein, one form of which circulates in the plasma and another form of which is a cell-surface protein mediating cellular adhesive interactions. Fibronectins are important components of connective tissue where they crosslink to collagen. Further, fibronectin is a protein involved in the aggregation of platelets.

In accordance with this invention fibronectin protein is adhered to an insoluble support matrix. An insoluble support matrix provides a biologically inert carrier system for the fibronectin so as to allow the fibronectin to be easily separated from a liquid phase. For convenience of separation, it is preferred that the support matrix be a water insoluble solid support matrix. Examples of suitable insoluble support matrixes include polystyrene beads; latex spheres; agarose dextran gel beads; glass slides, beads or well containers; filter paper; microtiter plates composed of polymer substrates; and plastic dip sticks.

Fibronectin protein can be adhered to the insoluble support matrix by a variety of means including surface adhesion or coating to the support matrix, covalent or affinity binding to the support matrix, or interstitial binding within a loosely woven matrix support.

Further in accordance with this invention the fibronectin component can be provided in a form wherein a quantity of treponemal immunogenic proteins is specifically reacted with the fibronectin. Fibronectin readily and selectively associates with treponemal immunogenic proteins, particularly treponemal proteins comprising the treponemal organism's outer membrane. A number of the treponemal protein immunogens have been identified, specifically termed protein P1 (89,500 daltons); P2 (29,500 daltons); P3 (25,500 daltons); P4 (20,000 daltons); P5 (59,000 daltons) and P6 (42,500 daltons). Purification and identification of these proteins are described by applicants' articles: "Surface-associated Host Proteins on Virulent *Treponema pallidum*," *Infect. Immun.* 26:1048-56 (1979); "Surface Characterization of Virulent *Treponema pallidum*", *Infect. Immun.* 30:814-23 (1980); and "Molecular Characterization of Receptor Binding Proteins and Immunogens of Virulent *Treponema Pallidum*", *J. Exp. Med.* 151:573-86 (1980) incorporated herein by reference. Further, Applicants have discovered that these purified proteins offer highly sensitive probes for the detection of anti-treponemal antibody, see e.g. "Enzyme-linked Immunosorbent Assay for the Detection of Serum Antibody to Outer Membrane Proteins of *Treponema pallidum*", *British J. Vener. Dis.* 59:75-9 (1983).

Within the context of this invention, either whole treponemal organisms or solubilized protein fractions of treponemes can be bound to the fibronectin component or provided as a separate component for subsequent binding to fibronectin. It is preferred however that the quantity of treponemal immunogenic proteins be provided in the form of a solubilized protein fraction as opposed to whole treponemal organisms.

In order that the invention may be more clearly understood, illustrative embodiments will be further described in terms of the following examples, which should not be construed to limit the scope of this invention.

A. Gelatin-Agarose purification of human plasma fibronectin.

1. A $1\frac{1}{2}\times 10$ cm column was prepared with gelatin-agarose (Sigma Chemical Co., St. Louis) and equilibrated with phosphate-buffered saline (PBS) supplemented with 0.05M cyclohexylaminopropane sulfonic acid (CAPS) prior to addition of fresh plasma obtained as outlined below. After addition of plasma diluted in CAPS and extensive washing of the column of unbound materials, fibronectin was eluted with 1.0M NaBr, 0.05M NaAC, pH 5.0. Eluted material was then dialyzed overnight against 4 liters of 0.1M NaCl, 0.01 M $CaCl_2$, and 0.05M CAPS, pH 11.0. The fibronectin was evaluated by sodium dodecylsulfate-polyacrylamide gel electrophoresis, and 99% purification of plasma fibronectin was achieved in this manner. Fibronectin was then aliquoted into small volumes into plastic tubes and frozen at −70° C. until further use.

2. Fifty ml of freshly drawn citrated human blood was centrifuged at 1000 rpm for 10 minutes. Plasma was decanted into sterile centrifuge tubes and re-centrifuged at 3000 rpm for 10 minutes. Fifteen ml of plasma was combined with an equal volume of 0.05M CAPS for processing in gelatin-agarose as above. The remaining plasma was frozen at −70° C. until further use.

B. Preparation of fibronectin-coated polyvinyl chloride microtiter wells.

1. Purified fibronectin was diluted no less than 1:5 in carbonate coating buffer (1.6 g/L $NaCO_3$, 3.0 g/L $NaHCO_3$, and 0.2 g/L $NaN_3$, pH 9.6), and 50 μl giving the appropriate amount of protein was aliquoted into individual wells of 96 well microtiter plates (Dynatech Labs). The plates were incubated overnight at 4° C. followed by washing once in PBS-1% bovine serum albumin (BSA). Finally, PBS-BSA was added to individual wells and plates stored at −20° C. until needed.

2. Fibronectin-coated wells were allowed to thaw at room temperature followed by an additional incubation for 60 minutes at 37° C. The wells were then washed at least 3 times with PBS and tapped dry. Varying amounts of *Treponema pallidum* detergent extract obtained as outlined below were then added and wells allowed to incubate for 60 minutes at room temperature. Fifty microliter volumes of solubilized *T. pallidum* extract were employed for experiments using serum reagents from experimental animals (rabbits and mice). Only 5 μl amounts of treponemal extract in 45 μl PBS were employed for experiments using sera from normal individuals and humans at various stages of infection with syphilis or other treponematosis.

3. Solubilization of T. pallidum organisms.

*T. pallidum* organisms ($1\times 10^{10}$ cell number) were obtained from testicular materials of infected rabbits. Treponemes were clarified from host materials, washed 3 times with PBS and stored at −70° C. until use. Pellets were resuspended in 0.5 ml NaCl-EDTA-Tris [NET; 150 mM NaCl, 5 mM disodium ethylenediaminetetraacetate (EDTA), and 5 mM tris (hydroxymethyl) amino-methane (Tris)] buffer, pH 7.4 containing 1% Zwittergent 3-12 detergent (Cal Biochem Co., La Jolla, Calif.) and 1 mM phenylmethylsulfonyl chloride (PMSF). The suspension was subjected to homogenization (10 strokes) followed by layering on a 5% sucrose cushion and centrifugation at $100{,}000\times g$ for 30 minutes. The supernatant containing solubilized *T. pallidum* proteins was diluted in NET+PMSF to give a 0.1% Zwittergent 3-12 concentration.

C. Use of *T. pallidum* antigens bound to fibronectin on microtiter plate wells for detection of antibody to syphilis and other treponematosis.

1. After addition of 50 μl of a solution containing soluble *T. pallidum* protein antigens to fibronectin-coated microtiter wells, the wells were incubated at room temperature for 60 minutes followed by washing 3 times with PBS. Control serum or serum from rabbits infected with *T. pallidum* was diluted in NET and 50 μl of diluted serum reagent added to wells. After a 60 minute incubation at 37° C., the wells were again washed 3 times with PBS followed by addition of 50 μl of indicator antibody (goat anti-rabbit immunoglobulin G) coupled to alkaline phosphatase (Miles Labs). Fifty μl p-nitrophenylphosphate was then added to extensively washed (3 times with PBS+3 times with distilled water) wells incubated 60 minutes at 37° C. After a 30 minute incubation at 37° C., the wells were examined spectrophotometrically at 405 nm for indication of enzyme activity. Values using serum from syphilitic animals were always greater than background values obtained using normal rabbit serum using the same serum dilutions. Results are tabulated in Table I.

TABLE I

Reactivity of rabbit syphilitic serum with *T. pallidum* materials absorbed to fibronectin coated microtiter plate wells

| | Absorbance (405 nm) | | | | |
|---|---|---|---|---|---|
| | NRS | | RSS | | |
| Experiment | 1:10 | 1:100 | 1:10 | 1:100 | 1:100 |
| 1. 50 ng Fibrorectin/well | | | | | |
| a. 50 µl Solubilized *T. pal*/well | .042 ± .015 | 0 | 1.337 ± .047 | >1.396 | 1.324 ± .08 |
| b. 200 µl Solubilized *T. pal*/well | .096 ± .018 | .037 ± .044 | 1.329 ± .06 | >1.359 | >1.309 |
| 2 100 ng Fibronectin/well | | | | | |
| a. 50 µl *T. pal*/well | .054 ± .009 | 0 | 1.253 ± .136 | >1.347 | 1.256 ± .099 |

NRS, normal rabbit serum; dilution in NET buffer
RSS, rabbit syphilitic serum

2. A similar protocol was employed when using sera from normal individuals, individuals having syphilis at different stages of infection or individuals having unrelated infections. Fifty µl of undiluted human serum was employed, and the incubation period was increased to 90 minutes at 37° C. The indicator antibody consisted of alkaline phosphatase-conjugated goat anti-human IgG. Serum from a patient with yaws, another syphilis-like infection caused by *T. pertenue*, was also employed similarly.

3. Substrate (p-nitrophenylphosphate) was prepared in standard diethanolamine buffer consisting of 9.7% diethanolamine, 0.2% NaN$_3$, 0.01% MgCl .6H$_2$O, pH 9.8. Results are tabulated in Table II.

TABLE II

Reactivity of Human Syphilitic Serum from Patients at Different Stages of Infection with *T. pallidum* Materials Absorbed to Fibronectin Coated Microtiter Well Plates

| Serum Sample/Stage of Infection | Absorbance (405 nm) |
|---|---|
| 1. Normal | .012 ± .002 |
| 2. Normal | .044 ± .006 |
| 3. Primary Syphilis | .080 ± .002 |
| 4. Latent Syphilis | .091 ± .018 |
| 5. Latent Syphilis | .200 ± .017 |
| 6. Yaws | .113 ± .005 |
| 7. Yaws | .289 ± .010 |
| 8. Group A streptococcus infection | .020 ± .005 |
| 9. Trichomoniasis | .030 ± .010 |

D. Results and unique features.

Results indicate that antibody responses by animals or humans infected with syphilis and other treponematoses can be detected using *T. pallidum* antigens adsorbed onto fibronectin-coated microtiter plate wells. The specificity of the reaction between fibronectin and *T. pallidum* molecules was demonstrated by gel electrophoretic analysis. Three prominent treponemal molecules, P1, P2 and P3 characterized as those responsible for the adherence properties of virulent spirochetes were found to bind to fibronectin with high affinity.

While the components and methods of this invention have been described in terms of preferred embodiments constituting the best mode known to Applicants at the time of this invention, it will be apparent to those of skill in the art that various changes may be made in the invention without departing from the scope thereof, which is defined by the following claims.

What is claimed is:

1. A diagnostic test pack for the detection of anti-*Treponema pallidum* antibodies, the pack comprising in packaged combination:
   (a) a first container of insolubilized fibronectin and antigenic outer membrane proteins extracted from *Treponema pallidum*, the proteins bound to the insolubilized fibronection so as to form a single component; and (b) a second container of (b) a second container of a quantity of indicator antibody sufficient for binding with the anti-*Treponema pallidum* antibody to be detected.

2. The test pack according to claim 1 wherein the indicator antibody is an enzyme linked antibody, a fluorescent tagged antibody, or a radiolabelled antibody.

3. The test pack according to claim 1 wherein the indicator antibody is an enzyme linked antibody and said pack further includes a third container of a quantity of substrate sufficient for binding with the enzyme to produce a visually detectable product.

4. The test pack of claim 1 wherein the insolubilized fibronectin comprises fibronectin insolubilized to beads, latex particles, glass slides, well containers, filter paper, microtiter plates, or plastic dip sticks.

5. The test pack of claim 1 wherein the antigenic *Treponema pallidum* proteins are outer membrane proteins P1, P2 or P3.

6. An immunoassay for the detection of anti-*Treponema pallidum* antibody present in a biological sample, the method comprising:
   (a) providing insolubilized fibronectin having bound thereto antigenic outer membrane proteins extracted from *Treponema pallidum* so as to form an insolubilized fibronectin, treponemal protein product;
   (b) contacting and incubating the insolubilized fibronectin, treponemal protein product for a sufficient time and with a sufficient quantity of the biological sample to permit binding reactions to occur between said insolubilized fibronectin, treponemal protein product and said biological sample; and
   (c) determining the presence of anti-*Treponema pallidum* antibody bound to the insolubilized fibronectin, treponemal protein product by contacting the insolubilized fibronectin, treponemal protein product with a quantity of indicator antibody sufficient for binding with the anti-*Treponema pallidum* antibody.

7. The method of claim 6 wherein the indicator antibody is an enzyme linked antibody, a fluorescent tagged antibody, or a radiolabelled antibody.

8. The method of claim 6 wherein the antigenic *Treponema pallidum* proteins are outer membrane proteins P1, P2 or P3.

9. A test component for a diagnostic test pack useful for the immunological detection of anti-*Treponema pallidum* antibody, the test component comprising: insolubilized fibronectin and antigenic outer membrane proteins extracted from *Treponema pallidum*, the proteins bound to the insolubilized fibronectin.

10. The test component of claim 9 wherein the insolubilized fibronectin comprises fibronectin insolubilized to beads, latex particles, glass slides, well containers, filter paper, microtiter plates, or plastic dip sticks.

11. The test component of claim 9 wherein the antigenic *Treponema pallidum* proteins are outer membrane proteins P1, P2 or P3.

* * * * *